(12) United States Patent
Erbstein et al.

(10) Patent No.: US 12,629,478 B2
(45) Date of Patent: *May 19, 2026

(54) DATA COLLECTION DEVICE FOR ATTACHMENT TO AN INJECTION DEVICE

(71) Applicant: Sanofi-Aventis Deutschland GMBH, Frankfurt am Main (DE)

(72) Inventors: Frank Erbstein, Frankfurt am Main (DE); Paul Richard Draper, Worcestershire (GB); Robert Frederick Veasey, Warwickshire (GB); David Aubrey Plumptre, Worcestershire (GB); Joseph Butler, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 6 days.

This patent is subject to a terminal disclaimer.

(21) Appl. No.: 18/785,158

(22) Filed: Jul. 26, 2024

(65) Prior Publication Data

US 2024/0382688 A1      Nov. 21, 2024

Related U.S. Application Data

(63) Continuation of application No. 17/574,449, filed on Jan. 12, 2022, now Pat. No. 12,070,584, which is a
(Continued)

(30) Foreign Application Priority Data

Feb. 19, 2015    (EP) ..................................... 15155758

(51) Int. Cl.
      *A61M 5/315*           (2006.01)
      *A61M 5/20*            (2006.01)
                                   (Continued)

(52) U.S. Cl.
      CPC ............ *A61M 5/3155* (2013.01); *A61M 5/20* (2013.01); *A61M 5/31568* (2013.01); *A61M 5/24* (2013.01);
                                   (Continued)

(58) Field of Classification Search
      CPC .................. A61M 5/3155; A61M 5/20; A61M 5/31568; A61M 5/24; A61M 2005/3126;
                                   (Continued)

(56) References Cited

U.S. PATENT DOCUMENTS

| | | | |
|---|---|---|---|
| 533,575 | A | 2/1895 | Wilkens |
| 4,959,056 | A | 9/1990 | Dombrowski et al. |

(Continued)

FOREIGN PATENT DOCUMENTS

| | | |
|---|---|---|
| CN | 101727540 | 6/2010 |
| CN | 102413855 | 4/2012 |

(Continued)

OTHER PUBLICATIONS

[No Author Listed], "Comparison of publication EP201012B1 with publication WO2010/098928," cited in European Opposition in EP Application No. 16729241.6, unknown date, 26 pages.

(Continued)

*Primary Examiner* — Isiaka O Akanbi
(74) *Attorney, Agent, or Firm* — Fish & Richardson P.C.

(57)                    ABSTRACT

A data collection device for attachment to an injection device, such as an injector pen, includes a sensor arrangement to detect movement of a movable component of the injection device relative to the data collection device during delivery of a medicament by the injection device, and a processor arrangement configured to, based on said detected movement, determine a medicament dosage administered by the injection device. The processor arrangement may monitor the time that has elapsed since the medicament dosage
(Continued)

was administered, and control a display to show the medicament dosage and elapsed time to provide a memory aid to the user. In an example embodiment, the sensor arrangement includes an optical encoder and the movable component includes a plurality of light barrier formations. The movable component may be a number sleeve that provides a visual indication of a dose programmed into the injection device.

20 Claims, 5 Drawing Sheets

Related U.S. Application Data continuation of application No. 16/806,810, filed on Mar. 2, 2020, now Pat. No. 11,278,677, which is a continuation of application No. 16/555,772, filed on Aug. 29, 2019, now Pat. No. 11,020,533, which is a continuation of application No. 15/551,971, filed as application No. PCT/EP2016/052987 on Feb. 12, 2016, now Pat. No. 10,420,895.

(51) Int. Cl.
  *A61M 5/24* (2006.01)
  *A61M 5/31* (2006.01)
(52) U.S. Cl.
  CPC ............... *A61M 2005/3126* (2013.01); *A61M 2205/3306* (2013.01); *A61M 2205/3317* (2013.01); *A61M 2205/3327* (2013.01); *A61M 2205/3561* (2013.01); *A61M 2205/50* (2013.01); *A61M 2205/502* (2013.01); *A61M 2205/52* (2013.01); *A61M 2205/581* (2013.01)
(58) Field of Classification Search
  CPC ............. A61M 2205/3306; A61M 2205/3317; A61M 2205/3327; A61M 2205/3561; A61M 2205/50; A61M 2205/502; A61M 2205/52; A61M 2205/581
  USPC ........................................ 356/315, 417, 132
  See application file for complete search history.

(56) References Cited

U.S. PATENT DOCUMENTS

| | | |
|---|---|---|
| 5,112,317 A | 5/1992 | Michel |
| 5,226,895 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,331,953 A | 7/1994 | Andersson et al. |
| 5,383,865 A | 1/1995 | Michel |
| 5,480,387 A | 1/1996 | Gabriel et al. |
| 5,505,704 A | 4/1996 | Pawelka et al. |
| 5,509,905 A | 4/1996 | Michel |
| 5,582,598 A | 12/1996 | Chanoch |
| 5,626,566 A | 5/1997 | Petersen et al. |
| 5,662,612 A | 9/1997 | Niehoff |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,246,322 B1 | 6/2001 | LeDain et al. |
| 6,248,095 B1 | 6/2001 | Giambattista et al. |
| 6,277,099 B1 | 8/2001 | Strowe et al. |
| 6,482,185 B1 | 11/2002 | Hartmann |
| 6,500,169 B1 | 12/2002 | Deng |
| 6,585,698 B1 | 7/2003 | Packman et al. |

| | | |
|---|---|---|
| 6,620,133 B1 | 9/2003 | Steck |
| 6,869,413 B2 | 3/2005 | Langley et al. |
| 6,899,698 B2 | 5/2005 | Sams |
| 6,936,032 B1 | 8/2005 | Bush, Jr. et al. |
| 7,008,399 B2 | 3/2006 | Larsen et al. |
| 7,241,278 B2 | 7/2007 | Moller |
| 7,749,186 B2 | 7/2010 | Kohlbrenner et al. |
| 8,052,655 B2 | 11/2011 | Moller et al. |
| 8,197,449 B2 | 6/2012 | Nielsen et al. |
| 8,231,573 B2 | 7/2012 | Edwards et al. |
| 8,556,847 B2 | 10/2013 | Kohlbrenner et al. |
| 8,556,865 B2 | 10/2013 | Krulevitch et al. |
| 8,556,866 B2 | 10/2013 | Krulevitch et al. |
| 8,556,867 B2 | 10/2013 | Krulevitch et al. |
| 8,560,271 B2 | 10/2013 | Koehler et al. |
| 8,613,719 B2 | 12/2013 | Karratt et al. |
| 8,672,899 B2 | 3/2014 | Diller et al. |
| 8,771,238 B2 | 7/2014 | Nielsen et al. |
| 8,994,382 B2 | 3/2015 | Nielsen et al. |
| 9,289,559 B2 | 3/2016 | Pedersen et al. |
| 9,522,238 B2 | 12/2016 | Nielsen et al. |
| 9,526,842 B2 | 12/2016 | Oh et al. |
| 9,623,188 B2 | 4/2017 | Nielsen et al. |
| 9,649,448 B2 | 5/2017 | Madsen |
| 9,672,328 B2 | 6/2017 | Saint et al. |
| 9,734,302 B2 | 8/2017 | Nielsen et al. |
| 9,959,391 B2 | 5/2018 | Saint et al. |
| 10,105,489 B2 | 10/2018 | Edwards et al. |
| 10,213,554 B2 | 2/2019 | Andersen et al. |
| 10,383,996 B2 | 8/2019 | Miller et al. |
| 10,446,269 B2 | 10/2019 | Groeschke et al. |
| 10,471,213 B2 | 11/2019 | Schabbach et al. |
| 10,483,000 B2 | 11/2019 | Saint et al. |
| 10,593,232 B2 | 3/2020 | Bauss |
| 10,617,827 B2 | 4/2020 | Hautaviita et al. |
| 10,695,504 B2 | 6/2020 | Nielsen et al. |
| 10,857,304 B2 | 12/2020 | Byerly |
| 10,874,802 B2 | 12/2020 | Toporek et al. |
| 11,424,026 B2 | 8/2022 | Groeschke et al. |
| 11,439,762 B2 | 9/2022 | Toporek et al. |
| 11,511,047 B2 | 11/2022 | Toporek et al. |
| 11,730,891 B2 | 8/2023 | Toporek et al. |
| 11,862,331 B2 | 1/2024 | Groeschke et al. |
| 11,944,796 B2 | 4/2024 | Toporek et al. |
| 12,027,259 B2 | 7/2024 | Groeschke et al. |
| 12,070,584 B2 * | 8/2024 | Erbstein ............ A61M 5/31568 |
| 12,283,373 B2 | 4/2025 | Groeschke et al. |
| 12,322,504 B2 | 6/2025 | Groeschke et al. |
| 2002/0052578 A1 | 5/2002 | Moller |
| 2002/0120235 A1 | 8/2002 | Enggaard |
| 2002/0123716 A1 | 9/2002 | VanDiver et al. |
| 2002/0143288 A1 | 10/2002 | Larsen et al. |
| 2002/0163435 A1 | 11/2002 | Kosaka |
| 2002/0188419 A1 | 12/2002 | Slate et al. |
| 2003/0036762 A1 | 2/2003 | Kerr et al. |
| 2003/0050609 A1 | 3/2003 | Sams |
| 2003/0139706 A1 | 7/2003 | Gray |
| 2003/0208113 A1 | 11/2003 | Mault et al. |
| 2004/0059299 A1 | 3/2004 | Moller |
| 2004/0085215 A1 | 5/2004 | Moberg et al. |
| 2004/0140972 A1 | 7/2004 | Hirota et al. |
| 2004/0210199 A1 | 10/2004 | Atterbury et al. |
| 2004/0254539 A1 | 12/2004 | Wolbring et al. |
| 2004/0267207 A1 | 12/2004 | Veasey et al. |
| 2005/0080384 A1 | 4/2005 | Green |
| 2005/0113765 A1 | 5/2005 | Veasey et al. |
| 2005/0151652 A1 | 7/2005 | Frasch |
| 2005/0182323 A1 | 8/2005 | Grispo et al. |
| 2005/0192530 A1 | 9/2005 | Castellano |
| 2005/0283065 A1 | 12/2005 | Babayoff |
| 2006/0135907 A1 | 6/2006 | Remde et al. |
| 2006/0153693 A1 | 7/2006 | Fiechter et al. |
| 2007/0123829 A1 | 5/2007 | Atterbury et al. |
| 2007/0210828 A1 | 9/2007 | Won et al. |
| 2007/0265579 A1 | 11/2007 | Kleyman et al. |
| 2008/0033369 A1 | 2/2008 | Kohlbrenner et al. |
| 2008/0058612 A1 | 3/2008 | Ohyu et al. |
| 2008/0262469 A1 | 10/2008 | Brister et al. |
| 2009/0043253 A1 | 2/2009 | Podaima |

(56)        References Cited

U.S. PATENT DOCUMENTS

| | | | |
|---|---|---|---|
| 2009/0069742 A1 | 3/2009 | Larsen | |
| 2009/0194104 A1 | 8/2009 | Van Sickle | |
| 2009/0275916 A1 | 11/2009 | Harms et al. | |
| 2010/0114026 A1 | 5/2010 | Karratt et al. | |
| 2010/0324496 A1 | 12/2010 | Plumptre et al. | |
| 2011/0037586 A1 | 2/2011 | Lu | |
| 2011/0112474 A1 | 5/2011 | Bochenko et al. | |
| 2011/0238017 A1 | 9/2011 | Watanabe et al. | |
| 2011/0270214 A1 | 11/2011 | Jorgensen et al. | |
| 2011/0313349 A1* | 12/2011 | Krulevitch | G16H 20/17 |
| | | | 604/65 |
| 2012/0092670 A1 | 4/2012 | Chatow et al. | |
| 2013/0197445 A1* | 8/2013 | Schabbach | G16H 20/17 |
| | | | 604/189 |
| 2013/0204227 A1 | 8/2013 | Bochenko et al. | |
| 2013/0274680 A1 | 10/2013 | Veasey et al. | |
| 2013/0310756 A1 | 11/2013 | Whalley et al. | |
| 2014/0005950 A1 | 1/2014 | Groeschke et al. | |
| 2014/0194826 A1 | 7/2014 | Nielsen et al. | |
| 2014/0194829 A1 | 7/2014 | Baek et al. | |
| 2015/0018775 A1 | 1/2015 | Groeschke et al. | |
| 2015/0202375 A1* | 7/2015 | Schabbach | A61M 5/31525 |
| | | | 604/207 |
| 2016/0235925 A1* | 8/2016 | Kuhn | A61M 5/24 |
| 2017/0182258 A1* | 6/2017 | Michael | G16H 20/17 |
| 2017/0189625 A1* | 7/2017 | Cirillo | A61M 5/3155 |
| 2017/0270276 A1* | 9/2017 | Saint | G16H 20/13 |
| 2017/0368263 A1* | 12/2017 | Ploch | A61M 5/31553 |
| 2018/0001027 A1* | 1/2018 | Klemm | A61M 5/31525 |
| 2018/0154086 A1 | 6/2018 | Toporek et al. | |
| 2019/0381248 A1 | 12/2019 | Erbstein et al. | |
| 2020/0013503 A1 | 1/2020 | Groeschke et al. | |
| 2020/0147315 A1 | 5/2020 | Toporek et al. | |
| 2020/0353176 A1 | 11/2020 | Toporek et al. | |
| 2020/0384205 A1 | 12/2020 | Toporek et al. | |
| 2021/0265053 A1 | 8/2021 | Groeschke et al. | |
| 2022/0001111 A1 | 1/2022 | Toporek et al. | |
| 2022/0246290 A1 | 8/2022 | Groeschke et al. | |
| 2022/0254484 A1 | 8/2022 | Groeschke et al. | |
| 2023/0256175 A1 | 8/2023 | Toporek et al. | |
| 2024/0066234 A1 | 2/2024 | Toporek et al. | |
| 2024/0087734 A1 | 3/2024 | Groeschke et al. | |
| 2025/0218584 A1 | 7/2025 | Groeschke et al. | |

FOREIGN PATENT DOCUMENTS

| | | |
|---|---|---|
| CN | 102413856 | 4/2012 |
| CN | 102458514 | 5/2012 |
| CN | 103458945 | 12/2013 |
| CN | 103561801 | 2/2014 |
| CN | 103648555 | 3/2014 |
| CN | 103702699 | 4/2014 |
| CN | 104203315 | 12/2014 |
| CN | 104245020 | 12/2014 |
| CN | 104363940 | 2/2015 |
| CN | 104411349 | 3/2015 |
| DE | 29904864 | 8/2000 |
| DE | 102004063664 | 7/2006 |
| EP | 0777123 | 6/1997 |
| EP | 0937471 | 8/1999 |
| EP | 0937476 | 8/1999 |
| EP | 2060284 | 5/2009 |
| EP | 2182456 | 5/2010 |
| EP | 2692378 | 2/2014 |
| EP | 2762184 | 8/2014 |
| EP | 3304372 | 12/2018 |
| EP | 2401012 | 4/2020 |
| EP | 2689359 | 11/2020 |
| JP | H11-267207 | 10/1999 |
| JP | 2000-506030 | 5/2000 |
| JP | 2001-087386 | 4/2001 |
| JP | 2001-509426 | 7/2001 |
| JP | 2004-523282 | 8/2004 |
| JP | 2008-516711 | 5/2008 |
| JP | 2009-530002 | 8/2009 |
| JP | 2010-534085 | 11/2010 |
| JP | 2012-500695 | 1/2012 |
| JP | 2012-504440 | 2/2012 |
| JP | 2012-135594 | 7/2012 |
| JP | 2012-519025 | 8/2012 |
| JP | 2012-519028 | 8/2012 |
| JP | 2014-516599 | 7/2014 |
| JP | 2014-520583 A | 8/2014 |
| JP | 2014-520584 | 8/2014 |
| JP | 2014-533537 | 12/2014 |
| WO | WO 1990/009202 | 8/1990 |
| WO | WO 1993/016743 | 9/1993 |
| WO | WO 1997/030742 | 8/1997 |
| WO | WO 1999/002210 | 1/1999 |
| WO | WO 1999/038554 | 8/1999 |
| WO | WO 2001/010484 | 2/2001 |
| WO | WO 2002/058767 | 8/2002 |
| WO | WO 2002/064196 | 8/2002 |
| WO | WO 2006/045525 | 5/2006 |
| WO | WO 2007/107564 | 9/2007 |
| WO | WO 2009/013736 | 1/2009 |
| WO | WO 2009/083600 | 7/2009 |
| WO | WO 2010/023303 | 3/2010 |
| WO | WO 2010/037828 | 4/2010 |
| WO | WO 2010/052275 | 5/2010 |
| WO | WO 2010/098927 | 9/2010 |
| WO | WO 2010/098928 | 9/2010 |
| WO | WO 2010/098931 | 9/2010 |
| WO | WO 2010/128493 | 11/2010 |
| WO | WO 2010/142598 | 12/2010 |
| WO | WO 2012/046199 | 4/2012 |
| WO | WO 2012/118687 | 9/2012 |
| WO | WO 2012/127046 | 9/2012 |
| WO | WO 2012/130703 | 10/2012 |
| WO | WO 2012/140097 | 10/2012 |
| WO | WO 2013/004843 A1 | 1/2013 |
| WO | WO 2013/004844 | 1/2013 |
| WO | WO 2013/010886 A2 | 1/2013 |
| WO | WO 2013/072445 | 5/2013 |
| WO | WO 2013/120774 | 8/2013 |
| WO | WO 2013/120776 | 8/2013 |
| WO | WO 2013/120777 | 8/2013 |
| WO | WO 2013/120778 | 8/2013 |
| WO | WO 2013/177135 | 11/2013 |
| WO | WO 2014/023763 | 2/2014 |
| WO | WO 2014/037331 | 3/2014 |
| WO | WO 2014/064691 | 5/2014 |
| WO | WO 2014/111337 | 7/2014 |
| WO | WO 2014/128156 | 8/2014 |
| WO | WO 2014/153599 A1 | 10/2014 |
| WO | WO 2014/173768 | 10/2014 |
| WO | WO 2014/173774 | 10/2014 |
| WO | WO 2014/180744 | 11/2014 |
| WO | WO 2014/180745 | 11/2014 |
| WO | WO 2016/131713 | 8/2016 |
| WO | WO 2016/193229 | 12/2016 |
| WO | WO 2019/173097 | 9/2019 |

OTHER PUBLICATIONS

[No Author Listed], "HumaPen Ergo Manual", Eli Lilly and Company Ltd., 2003, 2 pages.

[No Author Listed], "Technical Dossier for the HumaPen Pen-Injector Family," Eli Lilly & Company—Pharmaceutical Delivery Systems, Aug. 15, 2000, 17 pages.

Brief Communication in European Application No. 12710104.6, dated Jan. 20, 2022, 70 pages.

Brief Communication in European Application No. 12710104.6, dated Jan. 9, 2023, 47 pages.

Brief Communication in European Application No. 12710104.6, dated May 6, 2022, 37 pages.

Brief Communication in European Application No. 16704003.9, dated Jan. 21, 2022, 81 pages.

Brief Communication in European Application No. 16704003.9, dated May 3, 2022, 152 pages.

Brief Communication in European Application No. 16729241.6, dated Apr. 11, 2022, 28 pages.

(56)                    References Cited

OTHER PUBLICATIONS

Brief Communication in European Application No. 16729241.6, dated Apr. 7, 2022, 11 pages.
Brief Communication in European Application No. 16729241.6, dated Apr. 7, 2022, 22 pages.
Brief Communication in European Appln. No. 12710104.6, dated Mar. 13, 2023, 13 pages.
Decision Rejecting the Opposition in European Application No. 12710104.6, dated May 11, 2023, 62 pages.
dictionary.cambridge.org [online], "Button," 2014, retrieved on Jan. 3, 2022, retrieved from URL <https://dictionary.cambridge.org/de/worterbuch/englisch/button>, 11 pages.
EP Extended Search Report in European Patent Application No. 15171252.8, dated Dec. 9, 2015, 7 pages.
EP Notice of Opposition by Di-Care Zrt. in Patent Application No. 16704003.9, dated Aug. 27, 2021, 33 pages.
EP Notice of Opposition by Di-Care Zrt. in Patent Application No. 16729241.6, dated Feb. 8, 2021, 17 pages.
EP Notice of Opposition by Ferring International Center S.A. in Patent Application No. 9737825.1, dated Jun. 18, 2013, 22 pages.
EP Notice of Opposition by Herzog IP Patentanwalts GmbH in Patent Application No. 12710104.6, dated Aug. 31, 2021, 50 pages.
EP Notice of Opposition by Herzog IP Patentanwalts GMbH in Patent Application No. 16704003.9, dated Aug. 31, 2021, 126 pages.
EP Reply to a Submission in Opposition by Herzog IP Patentanwalts GMbH in Patent Application No. 12710104.6, dated Jan. 27, 2023, 162 pages.
EP Response to Communication in Opposition by Herzog IP Patentanwalts GMbH in Patent Application No. 16704003.9, dated Jun. 19, 2019, 7 pages.
EP Search Report for European Application No. 12710104.6, dated Sep. 21, 2017.
EP Search Report in European Patent Application No. 15155758.4, dated Sep. 4, 2015, 3 pages.
Examination Report in European Appln. No. 12710104.6, dated Sep. 21, 2017, 6 pages.
Interlocutory decision in Opposition Proceedings in European Application No. 16729241.6, dated Sep. 22, 2022, 231 pages.
International Preliminary Report on Patentability in Application No. PCT/EP2012/055252, dated Sep. 24, 2013, 9 pages.
International Preliminary Report on Patentability in International Appln. No. PCT/EP2016/052987, dated Aug. 22, 2017, 7 pages.
International Preliminary Report on Patentability in International Appln. No. PCT/EP2016/063139, dated Dec. 12, 2017, 7 pages.
International Search Report and Written Opinion in International Appln. No. PCT/EP2016/052987, dated Apr. 21, 2016, 10 pages.
International Search Report and Written Opinion in International Appln. No. PCT/EP2016/063139, dated Sep. 22, 2016, 12 pages.
International Search Report for International Application No. PCT/EP2012/055252, completed Oct. 31, 2012.
*Novo Nordisk A/S*, Plaintiff, v. *Sanofi-Aventis U.S. LLC and Sanofi-Aventis*, Defendants, Case No. 3:07-cv-03206-MLC-JJH, Affidavit of Charles E. Clemens, filed Sep. 10, 2007, 82 pages.
Novo Nordisk, "How to use NovoPen® 4," [No Publication Date Listed], 2 pages (English version).
Novo Nordisk, "Instruction Manual for the NovoPen® 4," 2004, 17 pages (Polish version).
Novo Nordisk, "Instruction Manual for the NovoPen® 4," 2004, 19 pages (Danish version).
OnDrugDelivery, "Delivering Injectables: Devices & Device Components," ONdrugDelivery Ltd., 2007, 20 pages.
Pearson et al., "Practical Aspects of Insulin Pen Devices," Journal of Diabetes Science and Technology, May 2010, 4(3):522-531.
Reply to Examination Report in European Appln. No. 12710104.6, dated Jun. 29, 2018, 6 pages.
Rustige, "Important New Safety Reminder Regarding the HumaPen Ergo", HumaPen Ergo Customer letter from Eli Lilly Canada, Dec. 11, 2001, 2 pages.
Written Submission in European Opposition in European Application No. 16729241.6, dated Apr. 4, 2022, 30 pages.
youtube.com [online], "Diabetes Education: How to Inject Insulin," available online as of Nov. 14, 2014, URL:< https://www.youtube.com/watch?v=ycp7BbFhG44>, 1 page [Video Submission].
youtube.com [online], "How to use SoloStar Pen for Injecting Lantus (Glargine) and Apidra (Glulisine) Insulin Music Version," available online as of May 17, 2013, URL:< https://www.youtube.com/watch?v=ZcfKG0Mp3kI>, 1 page [Video Submission].
youtube.com [online], "Injecting Insulin With the Lantus SoloSTAR Pen," available online as of Oct. 29, 2012, URL:< https://www.youtube.com/watch?v=g7JLG36ZO-U>, 2012, 1 page [Video Submission].
youtube.com [online], "NovoPen 5—Novo Nordisk," Youtube, Jul. 5, 2012, retrieved on Sep. 10, 2021, <https://www.youtube.com/watch?v=u3EX_0KzkQE>, 1 page [Video Submission].

* cited by examiner

DATA COLLECTION DEVICE FOR ATTACHMENT TO AN INJECTION DEVICE

CROSS REFERENCE TO RELATED APPLICATIONS

The present application is a continuation of U.S. patent application Ser. No. 17/574,449, filed on Jan. 12, 2022, which is a continuation of U.S. patent application Ser. No. 16/806,810, filed on Mar. 2, 2020, now U.S. Pat. No. 11,278,677, which is a continuation of U.S. patent application Ser. No. 16/555,772, filed on Aug. 29, 2019, now U.S. Pat. No. 11,020,533, which is a continuation of U.S. patent application Ser. No. 15/551,971, filed on Aug. 18, 2017, now U.S. Pat. No. 10,420,895, which is the national stage entry of International Patent Application No. PCT/EP2016/052987, filed on Feb. 12, 2016, and claims priority to Application No. EP 15155758.4, filed on Feb. 19, 2015, the disclosures of which are expressly incorporated herein in entirety by reference thereto.

TECHNICAL FIELD

The present disclosure relates to a data collection device for attachment to an injection device and collecting medicament dosage information therefrom.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin dose.

SUMMARY

According to one aspect, a data collection device includes a mating arrangement configured for attachment to an injection device, a sensor arrangement configured to detect movement of a movable dosage programming component of the injection device relative to the data collection device during delivery of a medicament, and a processor arrangement configured to, based on said detected movement, determine a medicament dosage administered by the injection device.

In this manner, the data collection device can collect medicament dosage information without relying on additional actions being made by a user and may improve the reliability of the recordal and logging of medicament administrations. In addition, the display of a previous dosage may act as a memory aid to the user when programming a subsequent dosage into the injector pen.

The sensor arrangement may include one or more of an optical sensor, a magnetic sensor, a capacitive sensor and a mechanical sensor. For example, the sensor arrangement may include an optical encoder unit. The processor arrangement may be configured to monitor a time period elapsed since a pulse was output by the optical encoder and to determine said medicament dosage if said time period exceeds a predetermined threshold. This may allow the end point of an injection stroke to be reliably identified. Alternatively, or additionally, the sensor arrangement may include mechanical switches and/or tracks for detecting the relative movement.

The processor arrangement may be configured to obtain time stamp information for the detected administration of the medicament dosage and to store the determined medicament dosage and said time stamp information, for example, to provide a log of administered injections. In this case, the data collection device may, optionally, include an output interface to allow the stored medicament dosage and time stamp information to be transmitted to an external device, such as a computer, through a communications link. The output interface may be configured for communications with the external device via a wired or wireless link.

Additionally, or alternatively, the processor arrangement may be configured to monitor an elapsed time after the detected administration, and to control a display to show the determined medicament dose and the elapsed time. By displaying such information, the data collection device may provide a further memory aid to the user.

In any of the above described arrangements according to this aspect, the data collection device may be attachable to a dosage programming component of the injection device, which is movable by a user to program a medicament dosage to be administered, so that the data collection device moves with the dosage programming component. In such an embodiment, the data collection device may be configured to allow the user to program the medicament dosage into the injector pen by gripping and moving the data collection device, instead of gripping and moving the dosage programming component. To facilitate such programming, the data collection device may be configured to provide a larger contact surface for the user's grip, when compared with the dosage programming component, or may include other formations that may allow a user to program the medicament dosage more easily. This may be particularly useful in instances where the user has limited dexterity.

In some embodiments, the data collection device is releasably attachable to the injection device. In other embodiments, the data collection device is permanently attachable to the injection device.

This aspect also provides a medicament administration apparatus comprising said data collection device and an injection device. An example of such a medicament administration apparatus may include an injection device comprising a movable dosage programming component, wherein the movable dosage programming component is configured to move as a medicament dosage is programmed into the injection device and a data collection device comprising an optical sensor, wherein the movable dosage programming component includes a plurality of light barriers.

The medicament administration apparatus may be configured so that the movable dosage programming component does not move relative to the data collection device during programming of a dose into the injection device. Such an arrangement may limit the relative movement to the period during delivery of a medicament so that it is not necessary for the processor arrangement to determine whether a dosage programmed into the injection device is increasing, e.g. during dosage programming, or decreasing, e.g. during dosage programming or during medicament delivery. In an embodiment where it is not necessary to discriminate between increasing and decreasing dosage levels, multiple sensors are not required. Hence, the sensor arrangement may be configured with a single sensor. This can provide a relatively simple apparatus and reduced data processing requirements when compared with sensor arrangements having multiple sensors.

The injection device and the data collection device may include formations that co-operate to attach the data collection device to the injection device. In some embodiments, one of a projection and a recess may be provided on the injection device and the other of the projection and the recess provided in the mating arrangement data collection device, for example, to provide a clip attachment or a snap-fit attachment.

In some embodiments, the injection device is a disposable injection device and the data collection device is configured to be releasably attachable to the injection device. In other embodiments, the injection device is a reusable injection device and the data collection device is permanently attached to the injection pen.

The injection device may be an injector pen.

BRIEF DESCRIPTION OF THE FIGURES

Example embodiments of the disclosure will now be described with reference to the accompanying figures, of which.

DETAILED DESCRIPTION

In the following, embodiments of the present disclosure will be described with reference to an insulin injection device. The present disclosure is however not limited to such application and may equally well be deployed with injection devices that eject other medicaments.

Figure 1:
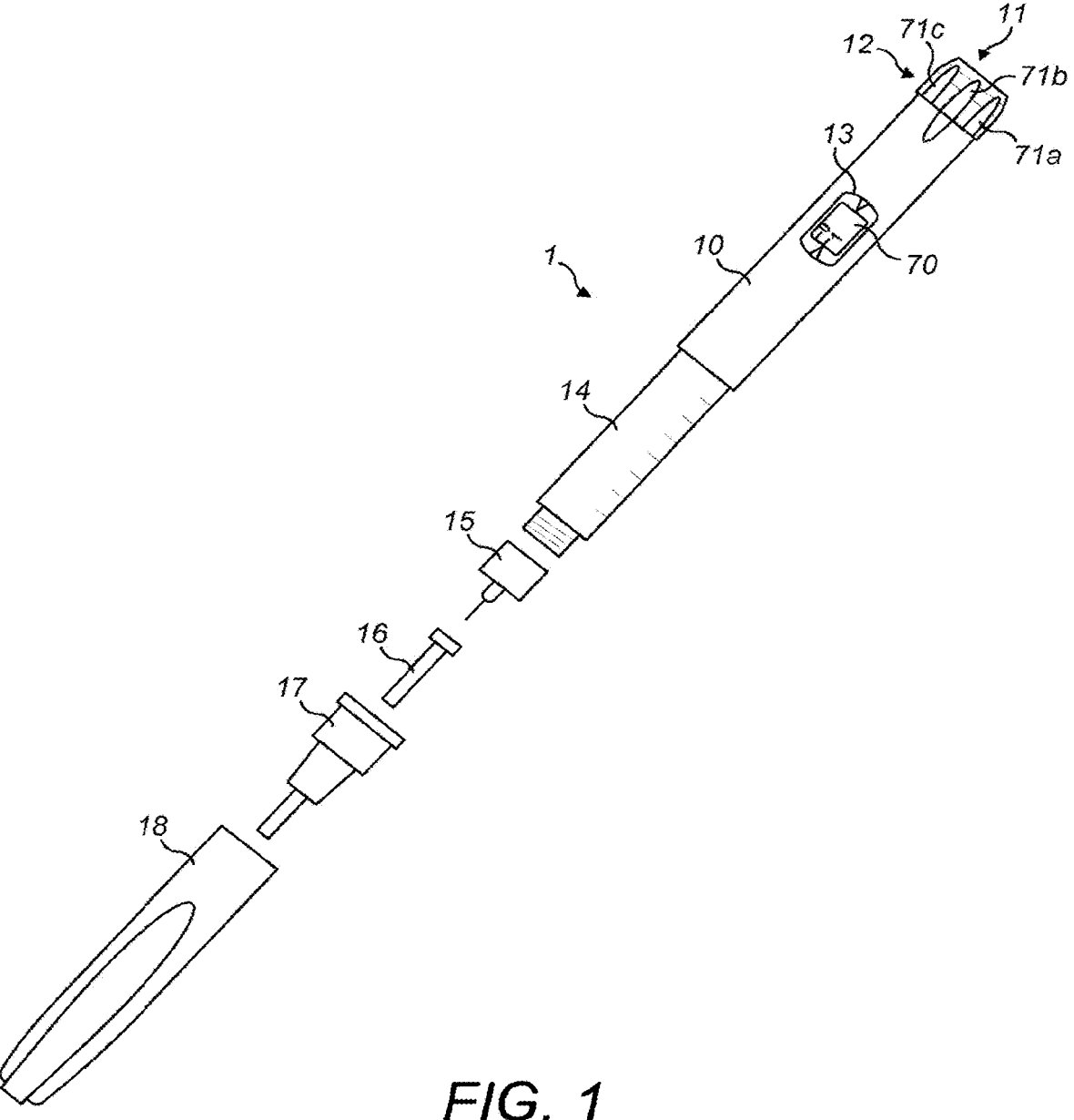
FIG. 1 shows an exploded view of an injection device for use with a data collection device according to an embodiment of the disclosure.

FIG. 1 is an exploded view of a medicament delivery device. In this example, the medicament delivery device is an injection device 1, such as Sanofi's SoloSTAR® insulin injection pen.

The injection device 1 of FIG. 1 is a pre-filled, disposable injection pen that includes a housing 10 and contains an insulin container 14, to which a needle 15 can be affixed. The needle is protected by an inner needle cap 16 and either an outer needle cap 17 other cap 18. An insulin dose to be ejected from injection device 1 can be programmed, or 'dialed in' by turning a dosage knob 12, and a currently programmed dose is then displayed via dosage window 13, for instance in multiples of units. For example, where the injection device 1 is configured to administer human insulin, the dosage may be displayed in so-called International Units (IU), wherein one IU is the biological equivalent of about 45.5 micrograms of pure crystalline insulin ($\frac{1}{22}$ mg). Other units may be employed in injection devices for delivering analogue insulin or other medicaments. It should be noted that the selected dose may equally well be displayed differently than as shown in the dosage window 13 in FIG. 1.

The dosage window 13 may be in the form of an aperture in the housing 10, which permits a user to view a limited portion of a number sleeve 70 that is configured to move when the dosage knob 12 is turned, to provide a visual indication of a currently programmed dose. The dosage knob 12 is rotated on a helical path with respect to the housing 10 when turned during programming.

In this example, the dosage knob 12 includes one or more formations 71a, 71b, 71c to facilitate attachment of a data collection device to be described herein below.

The injection device 1 may be configured so that turning the dosage knob 12 causes a mechanical click sound to provide acoustical feedback to a user. The number sleeve 70 mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose may also cause a mechanical click sound, which is however different from the sounds produced when using dosage knob 12.

In this embodiment, during delivery of the insulin dose, the dosage knob 12 is turned to its initial position in an axial movement, that is to say without rotation, while the number sleeve 70 is rotated to return to its initial position, e.g. to display a dose of zero units.

Injection device 1 may be used for several injection processes until either the insulin container 14 is empty or the expiration date of the medicament in the injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user. Nevertheless, differences (e.g. losses) between the ejected amounts and the injected doses may need to be taken into account.

Figure 2:
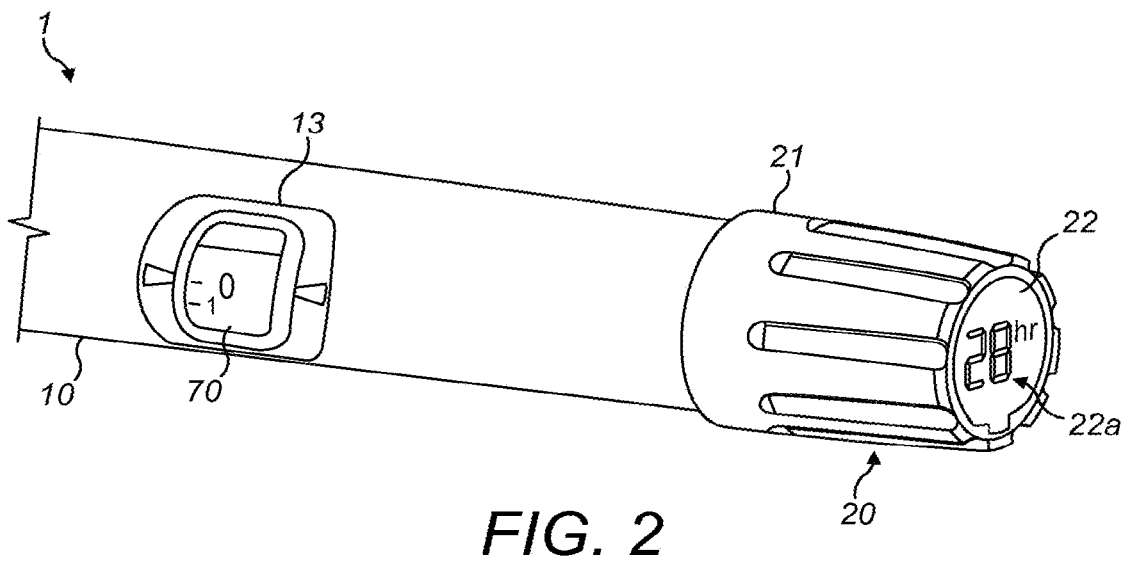
FIG. 2 depicts a data collection device according to an embodiment, attached to the injection device of FIG. 1.

FIG. 2 is a perspective view of one end of the injection device 1 when a data collection device 20 according to an example embodiment is attached. The data collection device 20 includes a housing 21 and a display 22 for presenting dosage information 22a.

Figure 3:
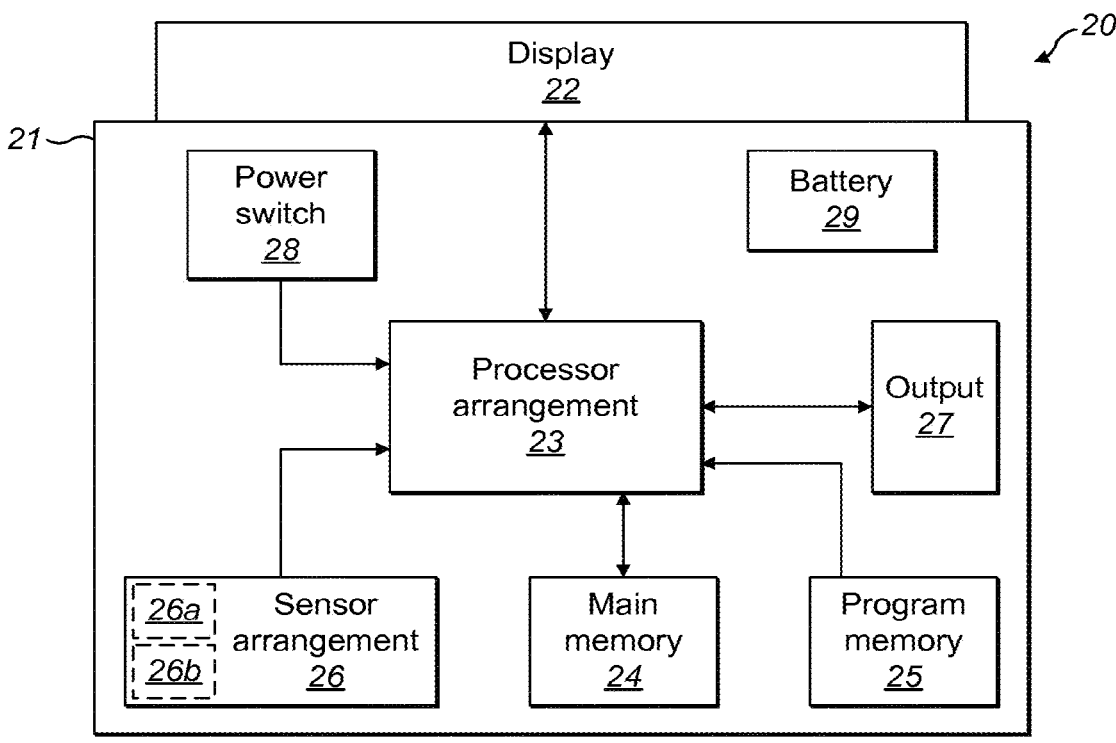
FIG. 3 is a block diagram of the data collection device shown in FIG. 2.

As shown in FIG. 3, the data collection device 20 also includes a processor arrangement 23 including one or more processors, such as a microprocessor, a Digital Signal Processor (DSP), Application Specific Integrated Circuit (ASIC), Field Programmable Gate Array (FPGA) or the like, together with memory units 24, 25, including program memory 24 and main memory 25, which can store software for execution by the processor arrangement 23.

A sensor arrangement 26, comprising one or more sensors, is provided. In this particular example, the sensor arrangement 26 is an optical encoder, including a light source 26a, such as a light emitting diode (LED) and a light detector 26b, such as an optical transducer.

An output 27 is provided, which may be a wireless communications interface for communicating with another device via a wireless network such as wi-fi or Bluetooth®, or an interface for a wired communications link, such as a socket for receiving a Universal Series Bus (USB), mini-USB or micro-USB connector.

A power switch 28 is provided, together with a battery 29. In one example, the power switch 28 is configured to respond to pressure applied to the display 22 by powering the data collection device 20 on or off.

Figures 4, 5:
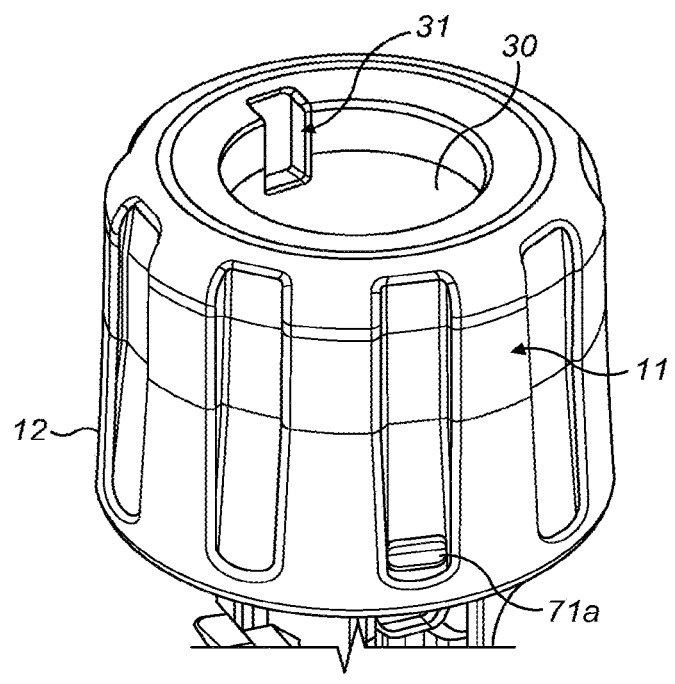
FIG. 4 is a perspective view of a portion of the injection device of FIG. 1.
FIG. 5 is a perspective view of a movable dosage programming component of the injection device of FIG. 1.

FIG. 4 shows the injection button 11 and dosage knob 12 of the injection device 1 in more detail. In this particular embodiment, the injection button 11 includes a cavity 30 on its upper surface, configured to receive at least a portion of the data collection device 20. In this example, a sidewall of the cavity 30 includes an aperture 31, through which a portion of the number sleeve 70 may be viewable.

FIG. 5 depicts the number sleeve 70. In this particular embodiment, castellations 72 are moulded onto one end of the number sleeve 70. One end of the number sleeve 70 is provided with castellations 72 that may act as light barriers for light emitted by the light source 26a.

In the particular example shown in FIG. 5, twelve castellations 72 are provided. The twelve castellations and the gaps between them have widths selected to provide 24 "edges", to correspond to dose increments up to a maximum dose 24 units shown on the number sleeve 70. The castellations 72 are formed using a material that has a reflectivity that differs from that of an inner surface of the injection button 11.

The number sleeve 70 is arranged to rotate helically along one direction as a dose is programmed into the injection device 1 using the dosage knob 12 and also to rotate helically in an opposite direction during delivery of a medicament dose by the injection device 1.

Figures 6, 7:
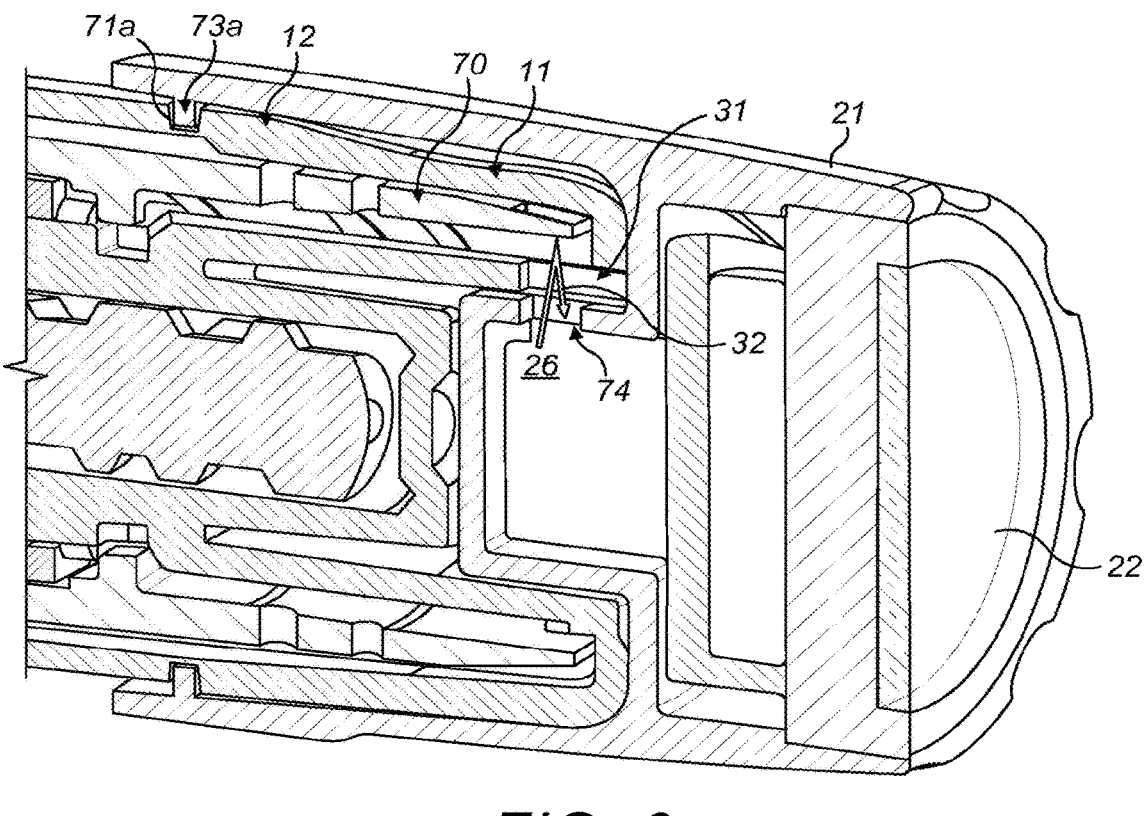
FIG. 6 is a cross-sectional view of portions of the data collection device of FIG. 3 and the injection device of FIG. 1 when attached together.
FIG. 7 is a graph showing an intensity of light received by a sensor arrangement in the data collection device of FIG. 3.

FIG. 6 is a cross-sectional view of part of the data collection device 20 and the injection device 1.

As shown in FIG. 6, the dosage knob 12 and the housing 21 of the data collection device 20 include co-operating formations 71a, 73a. In this particular embodiment, these formations are in the form of a projection 73a provided in the housing 21 of the data collection device 20 and a detent 71a provided in the dosage knob 12. As shown in FIG. 1, the formations 71a, 71b, 71c have only a limited extent, so that the data collection device 20 cannot rotate relative to the dosage knob 12 when attached.

Since the data collection device 20 and dosage knob 12 cannot rotate relative to one another, they move in concert as a dosage is programmed into the injection device 1. This may allow provision of a more ergonomic arrangement, since the data collection device 20 may provide a larger surface that can be gripped and rotated by the user during dosage programming. Alternatively, the data collection device 20 may be provided with formations on its outer surface to facilitate rotation of the data collection device 20 and, therefore, the dosage knob 12.

In arrangements where the data collection device 20 is to be releasably attachable to the injection device 1, the co-operating formations 71a, 73a may provide a clip-type arrangement that allows for easy removal of the data collection device 20. Such an arrangement may be useful where the data collection device 20 is to be used with disposable injection devices 1, since it allows the data collection device 20 to be removed from an injection device 1 and reused, or to allow a user with greater flexibility by being about to attach and remove the data collection device 20 at will.

Alternatively, the co-operating formations 71a, 73a may be configured to attach the data collection device 20 to the injection device 1 permanently, for example, using a "snap-fit". In other embodiments, the data collection device 20 maybe permanently attached in other ways, for example, through bonding. Such permanent attachments may be useful where the injection device 1 is reusable.

The number and/or positions of the co-operating formations 71a, 73a may be configured so that the data collection device 20 can only be attached to the injection device 1 in one particular position. In this particular example, the housing 21 of the data collection device 20 includes an aperture 74 through which light emitted by the light source 26a and light detected by the light detector 26b can pass when the data collection device 20 is in position. The co-operating formations 71a, 73a may be arranged so that, when the data collection device 20 is attached to the injection device 1, the aperture 74 in the housing 21 of the data collection device 20 is aligned with the aperture 31 in the sidewall of the cavity 30 in the injection button 11, as shown in FIG. 6.

As shown by the arrow 75 in FIG. 6, light emitted by the light source 26a thus passes through the apertures 74, 31 and into the injection button 11. If a castellation 72 of the number sleeve 70 is viewable through the aperture 31, then the light will be reflected from the castellation 72, and back through the apertures 31, 74, where it can be detected by the light detector 26b. Since the reflectivity of the castellations 72 differs from that of the inner surface of the injection button 11, the amount of light detected by the light detector 26b will depend on how much of a castellation 72 can be viewed through the aperture 31. In certain embodiments, the sensor arrangement 26 may be arranged to emit and/or detect only light with particular polarisation characteristics, in order to mitigate effects of stray light entering the aperture 74.

Figure 8:
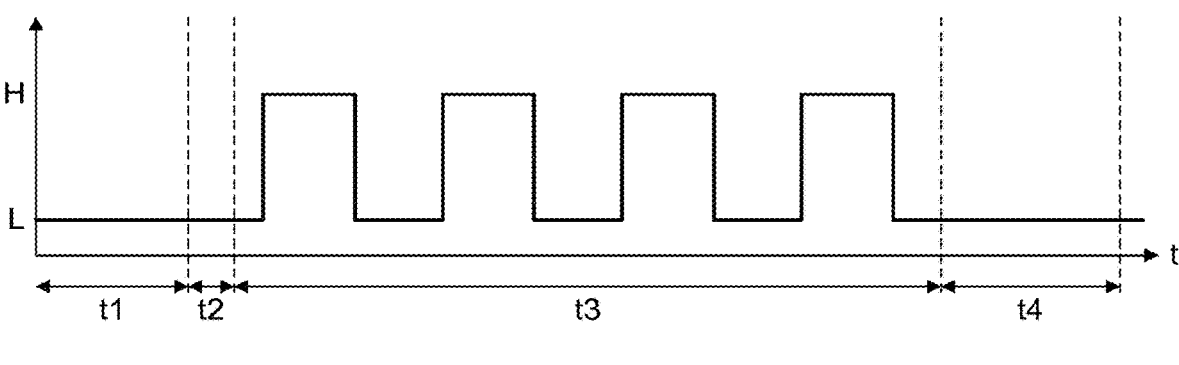
FIG. 8 is a graph showing an output of the sensor arrangement based on the received light intensities shown in FIG. 7.

FIG. 7 is a graph showing changes in the intensity of light received by the light detector 26b during programming and delivery of a medicament dose, while FIG. 8 is a graph showing an output that may be generated by the sensor arrangement 26 of this embodiment.

As noted above, while a dose is being programmed into the injection device 1, during time period t1 in FIGS. 7 and 8, the dosage knob 12 and the number sleeve 70 rotate helically. In this particular embodiment, since the data collection device 20 moves in concert with the dosage knob 12, the amount of light reflected back towards the light detector 26b should remain substantially constant, since there is little or no relative rotational movement between the number sleeve 70 and the data collection device 20. The amount of reflected light should also remain substantially constant between the completion of dosage programming and the start of the injection, shown as time period t2 in FIG. 7, since the number sleeve 70, dosage knob 12 and data collection device 20 are not being moved by a user.

The output of the sensor arrangement 26, shown in FIG. 8, is therefore substantially constant during time periods t1 and t2. The actual level of the output during time periods t1 and t2 will depend on whether a castellation 72 is viewable through the aperture 31 and, if so, how much of the aperture is covered by the castellation 72.

During the delivery of the medicament, shown as time period t3 in FIGS. 7 and 8, the number sleeve 70 rotates helically but the dosage knob 12 moves only axially, without rotating. Hence, the number sleeve 70 is rotating relative to the data collection device 20.

During time period t3, the castellations 72 of the number sleeve 70 will move across the aperture 31 as the number sleeve 31 rotates relative to the dosage knob 12 and data collection device 20, and the intensity of light received by the light detector 26b will vary accordingly, as shown in FIG. 7. In this particular example, the number sleeve 70 is more reflective than the inner surface of the injection button 11, and so the highest intensity levels shown in FIG. 7 correspond to positions where the amount by which the castellation 72 covers the aperture 31 is at its greatest.

The output of the light detector 26b during time period t3 will switch between a high and a low level, based on the received light intensity, as shown in FIG. 8. Since the edges of the castellations 72 correspond to increments in the medicament dosage, the processor arrangement 23 can determine an amount of medication delivered by the injection device based on the number of transitions between the high level and the low level in the output of the sensor arrangement 26.

The length of time period t3 will depend on the administered dosage and also on when the medicament delivery is deemed to be complete. When the medicament delivery is complete, the number sleeve 70 will cease to rotate relative to the dosage knob 12 and the data collection device 20, and the signal from the sensor arrangement 26 will stay at a substantially constant level.

In some embodiments, the processor arrangement 23 is arranged to monitor the time period that has elapsed from the last transition or the last pulse in the output of the sensor arrangement 24. When the elapsed time period reaches a predetermined threshold t4, the medicament delivery is considered to have been completed and the processor arrangement 23 proceeds with determining the medicament dose delivered to the user, based on the number of detected transitions in the output of the sensor arrangement during time period t3. In the particular example shown in FIGS. 7 and 8, there are eight transitions. Since the transitions correspond to the edges of the castellations which, in turn, correspond to the dosage increments in this particular embodiment, the determined medicament dose is 8 units.

The processor arrangement 23 then stores the determined medicament dose in main memory 24. The processor arrangement 23 may also store time stamp information, to provide a log recording delivery of medicament to the user.

The processor arrangement 23 may then power down the data collection device 20, in order to conserve battery power.

When the data collection device 20 is powered on again, by a user activating the power switch 28, the processor arrangement 23 may control the display to show the determined medicament dose information 22a, to aid the memory of the user. Optionally, the processor arrangement 23 may monitor an elapsed time since the determined medicament dose was delivered and control the display to show that elapsed time information too. For example, the processor arrangement 23 may cause the display 22 to switch periodically between displaying the determined medicament dosage information 22a and the elapsed time.

Figure 9:
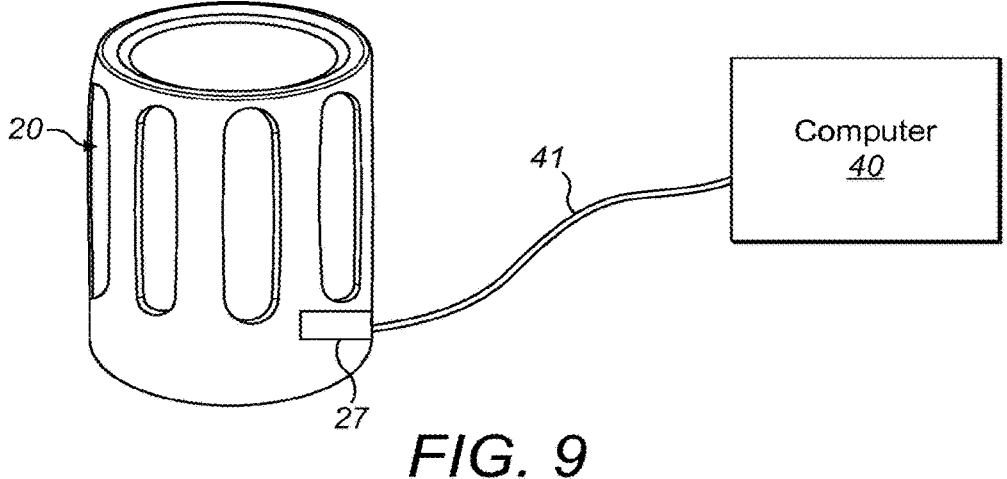
FIG. 9 depicts a system in which data from the data collection device of FIG. 3 is transmitted to another device.

The processor arrangement 23 may also transmit the determined medicament dosage and, where determined, the time stamp information to another device, such as a computer 40, as shown in FIG. 9. As noted above, the output 27 may be configured to transmit the information using a wireless communications link. Alternatively, the data collection device 20 may be connected to the computer 40 using a wired connection 41 to allow the information to be uploaded to the computer 40. The processor arrangement 23 may be configured to transmit the information to the computer 40 periodically.

The specific embodiments described in detail above are intended merely as examples of how the present disclosure may be implemented. Many variations in the configuration of the data collection device 20 and/or the injection device 1 may be conceived.

For example, it is not necessary that the formations provided on the number sleeve are in the form of castellations, nor is it necessary for the widths of the castellations and the gaps between them to correspond precisely to individual dosage increments, as in the above embodiment.

While the above described embodiment utilises an optical sensing arrangement 26, other types of sensors may be used as well as, or instead of, optical sensors. For example, the sensing arrangement may include a magnetic sensor, such as a Hall effect sensor. In such an example, one or more magnets may be mounted on the number sleeve, so that rotation of the number sleeve relative to the data collection device results in a varying magnetic field. In another example, a capacitive sensor may be used, where elements provided on the number sleeve may affect the capacitance between two plates provided in the data collection device. In other examples, mechanical sensors, with mechanical switches and/or tracks, may be used to detect the relative movement.

While the embodiment shown in FIG. 3 includes only one sensor, other embodiments may be devised in which the sensor arrangement includes multiple sensors of one or more types.

In the above described embodiments, the injection button 11 included a central cavity 30 for receiving at least part of the data collection device 20. In other embodiments, the central cavity may be omitted from the injection button if the data collection device 20 does not require one.

While the arrangement shown in FIG. 6 included co-operating formations in the form of a detent 71a in the dosage knob 12 and a projection 73a in the housing 21 of the data collection device 20, other types of co-operating formations or attachment methods may be used.

While the embodiments above have been described in relation to collecting data from an insulin injector pen, it is noted that embodiments of the disclosure may be used for other purposes, such as monitoring of injections of other medicaments.

What is claimed is:

1. A data collection device comprising:
   a housing;
   a mating arrangement configured for attachment to a dosage knob of an injection device such that the housing circumferentially surrounds at least a portion of an outer surface of the dosage knob and such that a user may grip and rotate the housing to cause the dosage knob to rotate in concert with the housing;

a magnetic sensor arrangement configured to detect a relative movement between a movable component of the injection device and the magnetic sensor arrangement; and a processor arrangement.

2. The data collection device according to claim 1, further comprising one or more of an optical sensor, a capacitive sensor, or a mechanical sensor.

3. The data collection device according to claim 1, wherein the magnetic sensor arrangement comprises at least one Hall effect sensor.

4. The data collection device according to claim 1, wherein the mating arrangement comprises a clip-type arrangement for attachment to the dosage knob.

5. The data collection device according to claim 1, wherein the mating arrangement is configured for attachment to the dosage knob using a snap-fit.

6. The data collection device according to claim 1, wherein the processor arrangement is configured to determine a medicament dosage administered by the injection device based at least on the detected movement.

7. The data collection device according to claim 6, wherein the processor arrangement is configured to obtain time stamp information for the administration of the medicament dosage and to store the determined medicament dosage and the time stamp information.

8. The data collection device according to claim 1, further comprising a wireless communications interface for wirelessly transmitting information to an external device.

9. The data collection device according to claim 8, wherein the information comprises a medicament dosage administered by the injection device.

10. The data collection device according to claim 1, wherein the processor arrangement is configured to monitor an elapsed time after a detected delivery of the medicament and to control an output based on the elapsed time.

11. The data collection device according to claim 1, further comprising a battery and a power switch configured to respond to pressure applied to the data collection device to power the data collection device on or off.

12. A medicament administration apparatus comprising:
an injection device comprising a movable component; and
a data collection device comprising:
  a housing;
  a mating arrangement configured for attachment to a dosage knob of the injection device such that the housing circumferentially surrounds at least a portion of an outer surface of the dosage knob and such that a user may grip and rotate the housing to cause the dosage knob to rotate in concert with the housing;
  a magnetic sensor arrangement configured to detect a relative movement between the movable component of the injection device relative and the magnetic sensor arrangement; and
  a processor arrangement.

13. The medicament administration apparatus according to claim 12, wherein the medicament administration apparatus is configured so that the movable component does not move relative to the data collection device during programming of a dose into the injection device.

14. The medicament administration apparatus according to claim 12, wherein the magnetic sensor arrangement is configured to detect the movement of the movable component during delivery of a medicament.

15. The medicament administration apparatus according to claim 12, wherein the injection device comprises at least one magnet coupled to the movable component, and wherein the magnetic sensor arrangement is configured to detect movement of the at least one magnet relative to the data collection device when the data collection device is attached to the injection device.

16. The medicament administration apparatus according to claim 12, wherein the data collection device is releasably attachable to the injection device.

17. The medicament administration apparatus according to claim 12, wherein the movable dosage programming component comprises a number sleeve.

18. The medicament administration apparatus according claim 17, wherein the number sleeve rotates helically in one direction as a dose is programmed into the injection device and rotates helically in an opposite direction during delivery of a medicament.

19. The medicament administration apparatus of claim 12, wherein the injection device comprises one or more of a disposable injection device, a reusable injection device, or an insulin injection device.

20. The medicament administration apparatus of claim 12, wherein the injection device comprises a medicament.

* * * * *